United States Patent [19]
Edwards, III

[11] 4,452,984
[45] Jun. 5, 1984

[54] OPTICALLY ACTIVE NICOTINE ANALOGS AND PROCESS FOR THEIR PREPARATION

[75] Inventor: William B. Edwards, III, Richmond, Va.

[73] Assignee: Philip Morris, Inc., New York, N.Y.

[21] Appl. No.: 377,989

[22] Filed: May 13, 1982

Related U.S. Application Data

[62] Division of Ser. No. 229,481, Jan. 29, 1981, Pat. No. 4,332,945.

[51] Int. Cl.$^3$ ............................................. C07D 401/04
[52] U.S. Cl. ..................................... 546/281; 546/282
[58] Field of Search ......................................... 546/281

[56] References Cited

PUBLICATIONS

Morrin et al., Chem. Abstracts, vol. 93, No. 13, Item 93-132, 669e, Sep. 29, 1980.
March, Advanced Organic Chemistry, Second Edition, pp. 108–111, McGraw-Hill Pub., 1977.
Hecht et al., Journal of Medicinal Chem., vol. 23, No. 10, pp. 1175–1178, Oct. 1980.
Castonguay et al., Journal of Organic Chem., vol. 44, No. 24, pp. 4332–4337, (1979).
Titus et al., Chemical Abstracts, vol. 76, No. 1, Item No. 1928q, Jan. 3, 1972.
Chemical Abstracts, Ninth Collective Index, vols. 76-85, Formulas $C_9H_{13}BrS-C_{12}H_{10}N_2O_2Zr$, (1976).

*Primary Examiner*—Alan L. Rotman
*Attorney, Agent, or Firm*—A. I. Palmer; George E. Inskeep

[57] ABSTRACT

This invention provides a process for the preparation of cotinine and nicotine analogs containing substituents on pyrrolidinone/pyrrolidine ring at the 3' position of cotinine and at the 4' and 5' position of nicotine.

The process proceeds via a first step preparation of a cotinine intermediate which is represented by the formula:

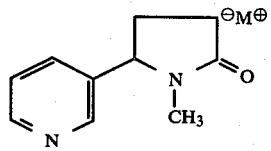

wherein M is an alkali metal cation.

8 Claims, No Drawings

OPTICALLY ACTIVE NICOTINE ANALOGS AND PROCESS FOR THEIR PREPARATION

This is a division of application Ser. No. 229,481, filed Jan. 29, 1981, now U.S. Pat. No. 4,332,945, issued June 1, 1982.

BACKGROUND OF THE INVENTION

1. Field of the Invention

The present invention relates to a novel process for the preparation of enantiomerically pure cotinine and nicotine analogs containing substituents on the pyrrolidinone/pyrrolidine ring at the 3' position of cotinine and at the 4' and 5' position of nicotine. The invention also relates to the compounds which are useful as insecticides.

2. Description of the Prior Art

Nicotine has been used as an insecticide for many years. Yamamoto has studied a number of nicotinoids (both natural and synthetic) with regard to their insecticidal activity [*Agr. Biol. Chem.*, 26, 709 (1962); Id., 27, 445 (1963); Id., 27, 450 (1963), Id., 27, 684 (1963); Id., 32, 568 (1968); Id., 32, 747 (1968); Id., 32, 1341 (1968)]. Several of the analogs studies possessed significant toxicity towards aphids, house flies, and cockroaches. Individual enantiomers of nicotinoids have been shown to display wide differences in insecticidal activity [Richardson, C., Craig, L., and Hansberry, R., *J. Econ. Entomol.*, 29, 850 (1936); Hansberry, R., and Norton L., Id., 33, 734 (1940)]. For example, d-nicotine was found to be five times less effective against aphids than the natural l-nicotine. Further differences in insectidal activity between individual enantiomers and their racemic mixtures were demonstrated: the racemic mixture, d, l-nicotine, was half as potent against aphids as l-nicotine and the racemic mixture, d, l-nornicotine, was less potent against aphids than either of its enantiomeric components although the individual d- and l-nornicotine enantiomers possessed comparable toxicity against aphids. Clearly, the optical activity of a given nicotinoid is important to its biological properties and methods for the production of nicotinoids having specific optical activity are of considerable interest.

Various methods have been suggested for the chemical and biological resolution of racemic nicotine. Soeda, Y., and Yakamoto, *Botyn-Kaga Ku*, 34, 57 (1969); Chem. Ab. 42:6364d (abstract of article by Gol'dfarb, et. al., *Izvest. Akad. Nauk S.S.S.R. Otdel. Khim Nauk* 1946, 557); and Yamashita, et. al., "Microbial Resolution of d,l-Nicotine", *Nippon Nogei Kagaku Kaisha*, Vol. 37, No. 7, pp. 385–388 (July 1963). Other generally known methods for preparing optically pure nicotine analogs include chemical transformation of l-nicotine to yield optically pure analogs, microbial transformation of nicotine or nicotinoids to yield optically pure analogs, and chemical transformations of optically pure nicotine analogs. For example, Bowman and McKennis, "(−)-Continine", *Biochem, Prep.*, 10, 35 (1963) [hereinafter cities as "Bowman and McKennis"] describes procedures for converting optically pure nicotine to optically pure cotinine.*

*S-cotinine is a known metabolite of S-nicotine. Morselli, et. al., *J. Med. Chem.*, 10, pp. 1033–36 (1967)

Sanders, et. al., "Nicotine Chemistry 5'-Cyanonicotine", *J. Org. Chem.*, 40, 19, pp. 2848–49 (1975) [hereinafter cited as "Sanders"] discloses the preparation of an inseparable mixture of (2'S)-cis-and-trans-5'cyanonicotine from (S)-cotinine, using the method of Bowman and McKennis for the preparation of (S)-cotinine. Acid hydrolysis of the nitrile mixture and fractional crystallization produced (2'S)-cis-nicotine-5'-carboxylic acid and (2'S)-trans-nicotine-5'-carboxylic acid.

Leete, "A Systematic Degradation of Nicotine to Determine Activity at C-2' and C-5'", *J. Org. Chem.*, 41, 21, pp. 3438–441 (1976) [hereinafter cited as "Leete"] shows preparation of (2'S)-cis and trans-5'-phenylnicotine from (5'S)-cotinine. The method disclosed comprises reacting phenyllithium with cotinine in tetrahydrofuran at −78° C., acidifying the resulting mixture with HCl, and reducing the acidified mixture with NaCNBH$_3$ or NaBH$_4$. Reduction with NaBH$_4$ afforded a greater proportion of the trans isomer compared to the ratio of isomers produced by NaCNBH$_3$ reduction.

McKennis, et. al., "The Synthesis of Hydroxycotinine and Studies On Its Structure", *J. Org. Chem.*, 28, pp. 383–85 (1963), discloses racemic 3'-acetamidocotinine and the derivatives, 3'-aminocotinine (produced by acid hydrolysis of the acetamido compound), hydroxycotinine (indicated to be 3'-hydroxycotinine, produced by diazotization of the aminocotinine), and chlorocotinine (presumed to be 3'-chlorocotinine, produced by reacting the high-melting isomer of the hydroxycotinine with thionyl chloride).

Dagne and Castagnoli, "Structure of Hydroxycotinine, a Nicotine Metabolite", *J. Med. Chem.*, 15, 4, pp. 356–360 (1972) suggests two synthetic methods for the synthesis of cis- and trans-isomers of 3-hydroxy-1-methyl-5-(3-pyridyl)-2-pyrrolidinone. One approach described comprises hydrogenolysis of an isoxazolidine of pyridine which approach has the advantage that the reaction proceeds with retention of configuration at C-3 and C-5 of the isoxazolidine ring. Analysis of the products of both of the synthetic methods pursued established the synthetic products to be cis-3-hydroxy-1-methyl-5-(3-pyridyl)-2-pyrrolidinone and trans-3-hydroxy-1-methyl-5-(3-pyridyl)-2-pyrrolidinone.

Dagne and Castagnoli also describe preparation of the corresponding mesylate (—OSO$_2$CH$_3$) and acetoxy (—OCOCH$_3$) compounds. Also see Dagne, et. al., "Deuterium Isotope Effects in the 'in Vivo' Metabolism of Cotinine", *J. Med. Chem.*, 17, 12, pp. 1330–33 (1974).

McKennis, et. al., "Demethylation of Cotinine 'in Vivo'", *J. Am. Chem. Soc.*, 81, pp. 3951–54 (1959) shows reduction of (−)-cotinine with lithium aluminum hydride in tetrahydrofuran under reflux conditions to form (−)-nicotine and prepared the acetate of impure 2'S, 4'R-4'-hydroxycotinine (obtained from the metabolism of S-cotinine by dogs) by acetylation.

Duffield, et. al., "Mass Spectrometry in Structural and Stereochemical Problems, LXXII, A Study of the Fragmentation Processes of Some Tobacco Alkaloids", *J. Am. Chem. Soc.*, 87, 2926–932 (1965) prepared 4',4'-dibromocotinine from nicotine by bromination in a glacial acetic acid-water mixture. Heating cotinine with potassium carbonate-deuterium oxide generated cotinine-4',4'-d$_2$. Lithium aluminum hydride reduction of this material yielded nicotine-4',4'-d$_2$.

Overman, et. al., *J. Am. Chem Soc.*, 101, pp. 1310–12 (1979) describes the reaction of aldehydes and salts of 2-alkoxy-3-butenamines to form substituted 3-acylpyrrolidines, in a single step and discloses an acyl compound having the formula:

Tepehmbeb, et al., *Zh. Obscher Khimii*, 33, 12, pp. 4006–011 (1963) discloses a compound having the formula:

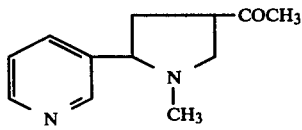

Wasserman, et al., "Reactions of Lithium Enolates With Molecular Oxygen", *Tet. Letters*, 21, pp. 1731–34 (1975) describes a method for α-hydroxylation of N,N-dialkyl amides using lithium diisopropylamide to generate carbanions of the dialkylamide followed by rapid oxidation of the carbanion formed and reducing the resulting hydroperoxide to form the α-hydroxylated amide. The following conversion is disclosed:

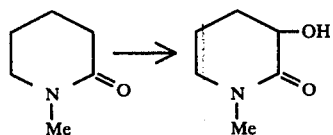

Rueppel & Rapport *J. Am. Chem. Soc.*, 93, pp. 7021–28 (1971) describe the preparation of various "unnatural precursors" for the biosynthesis of nicotine analogs. A premise of the study was that it is easier to synthesize a substituted precursor and biosynthesize "unnatural" nicotine analogs than to carry out a total synthesis of an analog of a natural product. The following reaction schemes are disclosed:

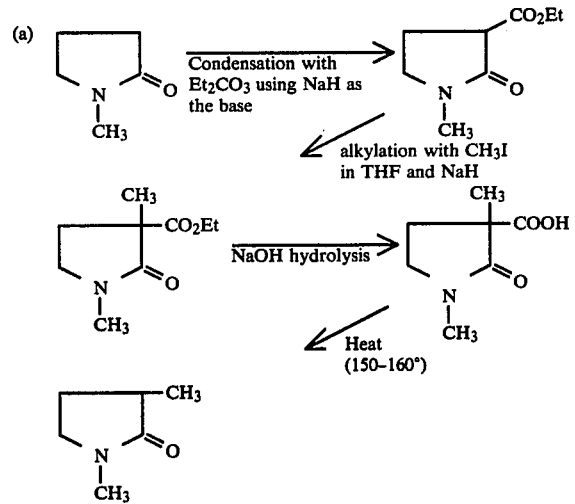

Rueppel and Rapport prepared 1,3,3-trimethyl-2-pyrrolidinone by alkylating 1-methyl-2-pyrrolidinone with 2.8 equivalents of methyl iodide in diethyl ether with lithium diisopropylamide as the base.

SUMMARY OF THE INVENTION

The present invention concerns a process for the preparation of nicotine analogs, and particularly concerns a process for the preparation of optically pure 3- and 3,3-substituted (5S)- and (5R)-1-methyl-5-(3-pyridyl)-2-pyrrolidinones (2S)- and (2R) and 4-, 4,4-, 4,5-, 4,5,5-, 4,4,5- and 4,4,5,5-substituted-1-methyl-2-(3-pyridyl)pyrrolidines. Also disclosed are methods for the preparation of optically pure 3- and 3,3-substituted (3S,5S)-, (3R,5S)-, (3S,5R)-, (3R, 5S)-, (5S)-, and (5R)-1-methyl-5-(3-pyridyl)-2-pyrrolidinones and 4-, 4,4-, 4,5-, 4,5,5-, 4,4,5- and 4,4,5,5-substituted (2S,4S)-, (2S,4R)-, (2R,4S)-, (2R,4R)-, (2S)- and (2R)-1-methyl-2-(3-pyridyl)pyrrolidines. The compounds of the present invention may be represented by the following formulae:

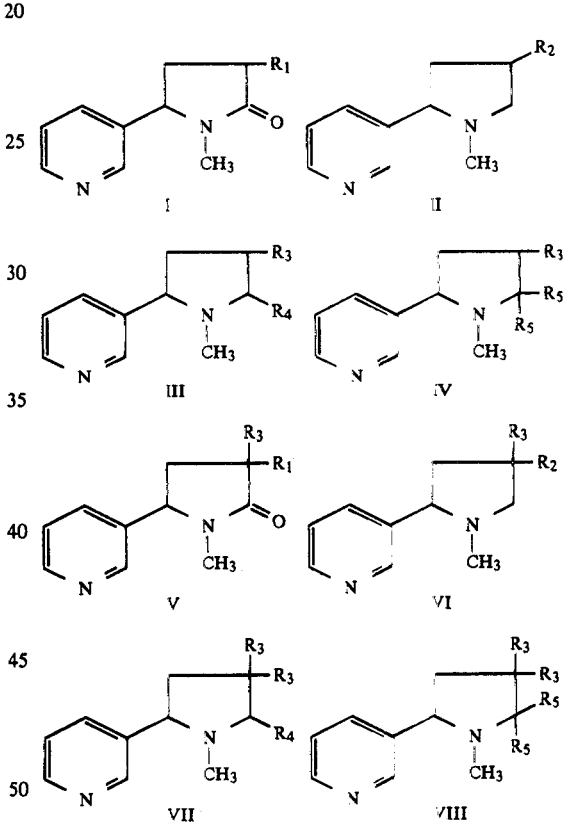

wherein $R_1 = CO_2R_6$ [$R_6$ = alkyl, cycloalkyl, aryl]; or alkyl; $R_2 = CH_2OH$ or alkyl; $R_3 =$ alkyl; $R_4 =$ alkyl; cycloalkyl, aryl, $-CN$, $-CONH_2$, $-CO_2H$, or $CO_2R_7$ [$R_7 =$ alkyl, cycloalkyl or aryl]; and $R_5 =$ alkyl, cycloalky or aryl.

The term "alkyl" used in connection with the foregoing formulae is meant to include straight chain or branched alkyl groups with 1 to 12 carbon atoms such as methyl, ethyl, propyl, isopropyl, butyl, pentyl, hexyl, 2-ethylhexyl, octyl, isooctyl, decyl, dodecyl, and the like.

The term "cycloalkyl" is meant to include cycloalkyl groups with 3 to 12 carbon atoms such as cyclopropyl, cyclobutyl, cyclopentyl, cyclohexyl, methylcyclohexyl, hexylcyclohexyl, cyclohexylmethyl, cycloheptyl, and the like.

The term "aryl" is meant to include aromatic groups with 6 to 12 carbon atoms such as phenyl, tolyl, xylyl, ethylphenyl, phenethyl, fluorophenyl, pyridyl, pyrazyl, naphthyl, and the like.

The compounds within the scope of formulae I–VIII have at least one basic nitrogen atom and can therefore form acid addition salts with inorganic or organic acids, for example, hydrochloric acid, acetic acid, maleic acid, p-toluenesulfonic acid, ethanesulfonic acid and the like. The salts of these compounds can also be in the form of hydrates (e.g., mono-, di-, tri-, or polyhydrates).

The present invention also concerns a new and improved process for the preparation of (2S,4S)-, (2S,4R)-, (2R,4S)-, and (2R,4R)-4-hydroxymethyl-1-methyl-2-(3-pyridyl)pyrrolidines of high optical purity. Also disclosed are methods for the preparation of (3S,5S)-, (3R,5S)-, (3S,5R)-, and (3R, 5R)-3-hydroxy-1-methyl-5-(3-pyridyl)-2-pyrrolidinones and (2R,4S)-, (2S,4R)-, (2R,4S)-, and (2R,4R)-4-hydroxy-1-methyl-2-(3-pyridyl)pyrrolidines of high optical purity.

In one aspect, this invention provides a one-step process for preparing a cotinine compound represented by the formula:

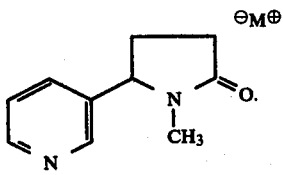

A wherein M is an alkali metal cation, which comprises reacting cotinine with a non-nucleophilic alkali metal base in an aprotic solvent medium at a temperature in the range between about −120° and 180° C.

In another aspect, this invention provides a two-step process which comprises preparing the cotinine derivative A in the manner described, and thereafter reacting derivative A with an organic compound which is capable of condensing with the cotinine carbanion to yield a 3-substituted cotinine compound.

The term "non-nucleophilic" alkali metal base refers to strong base of the alkali metal hydride type such as alkali metal amides and alkali metal hydrocarbyls. Illustrative of such bases are sodium hydride, lithium diisopropylamide, phenyllithium, and the like.

The term "aprotic" refers to any solvent which substantially does not yield a proton, and which is substantially inert under the reaction conditions of the invention process.

More specifically, the novel compounds of the present invention are prepared according to the present invention using optically pure cotinine as the starting material. Compounds of formula I are prepared by condensing the cotinine with about one equivalent of a compound selected from the group consisting of $(R_5)_2CO_3$ [$R_5$ being defined above], and alkyl halides using a non-nucleophilic base such as lithium diisopropylamide or sodium hydride to form the correspondingly optically pure 3-substituted-1-methyl-5-(3-pyridyl)-2-pyrrolidinone. Temperatures employed may range from −110° to 180° C., with a preferred range of −78° to 85° C. Suitable alkyl halides include methyl iodide, ethyl iodide, ethyl bromide, and the like. Compounds of formula I wherein $R_1$=alkyl may be converted to compounds of formula III by the methods disclosed for the conversion of cotinine to 5-substituted nicotines disclosed in Leete or Sanders, supra. The compounds of formula III wherein $R_4$ is $-CO_2R_7$ may be prepared by esterification of compounds of formula III wherein $R_4$ is $-CO_2H$. The compounds of formula III wherein $R_4$ is $-CONH_2$ may be prepared by heating the ammonium salt of the carboxylic acid (formula III, $R_4=CO_2H$) or by the reaction of $NH_3$ with the acid chloride of the carboxylic acid.

Compounds of formula IV are prepared by reacting a compound of formula I wherein $R_1$ is an alkyl group with a reagent selected from the group consisting of RLi or RMgX where R=$R_5$ of formula IV and RMgX signifies a Grignard reagent.

Compounds of formula V are prepared by condensing a compound of formula I wherein $R_1$ is an alkyl group in the same manner described for the preparation of formula I compounds from cotinine. Similarly, compounds of formulae VII and VIII are prepared from compounds of formula V wherein $R_1$ is alkyl in the same manner described for the preparation of formula III and formula IV compounds, respectively.

Substituted nicotines of formula II and VI are prepared from formula I and formula V compounds, respectively, by reduction of the carbonyl group by methods known in the art. Reduction with alkali metal hydrides or hydride complexes is preferred. This type of treatment will also convert any ester substituents at the 3-position of the pyrrolidinone ring to $-CH_2OH$. See Example 2, infra.

The following examples are illustrative but not limiting of the present invention. Temperatures are in degrees centigrade. The S-(−)-cotinine employed in the experiments was prepared from S-(−)-nicotine using the method of Bowman and McKennis, supra.

The δ values for all NMR spectra are relative to internal tetramethylsilane. All TLC and preparative TLC were run on Silica gel GF plates. All GLC and preparative GLC were run on a 5′×¼″SS column packed with 5% SE-30 on Chromosorb G HP (80–100 mesh) and with helium carrier gas at 60 mL/min. Abbreviations used are as follows: GLC=gas layer chromatography; HPLC=high pressure liquid chromatography; TLC=thin layer chromatography; $N_2$=nitrogen; $Et_2O$=ethyl ether; $CH_2Cl_2$=dichloromethane; $CD_2Cl_2$=deutrodichloromethane; $CHCl_3$=chloroform; $CDCl_3$=deutrochloroform; NMR=nuclear magnetic resonance; HCl=hydrogen chloride; NaOH=sodium hyroxide; $NH_4OH$=ammonium hydroxide; anhyd=anhydrous; mL=milliliter(s); g=gram(s); mmol=millimole(s); mol=-mole(s); min=minute(s); hr=hour(s); $Na_2SO_4$=sodium sulfate; $CaCl_2$=calcium chloride; EtOH=ethanol; MeOH=methanol; EtOAc=ethyl acetate. Nomenclature for the pyrrolidinones (A) and pyrrolidines (B) are based on the following numbering system:

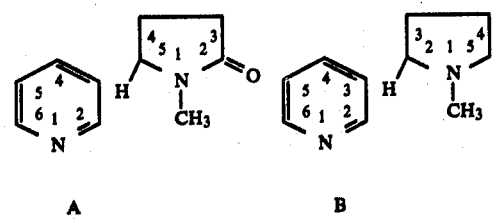

A        B

If the syntheses are carried out using R-(+)-cotinine (prepared from R-(+)-nicotine), then the following would occur:

1. For all pyrrolidinone compounds 5S becomes 5R.
2. For all pyrrolidine compounds 2S becomes 2R.
3. The structure of all products is the mirror image of those obtained.
4. The 2S, 4S, and 2S, 4R compounds become 2R, 4R, and 2R, 4S compounds respectively.
5. The 3S, 5S and 3R, 5S compounds become 3R, 5R and 3S, 5 R compounds respectively.
6. The 3RS, 5S and 2S, 5RS mixtures become 3RS, 5R and 2R, 5RS mixtures respectively.
7. The NMR spectra do not change for related sets (e.g., 2S, 4S vs 2R, 4R).
8. The sign of the optical rotation changes for related sets (e.g., 2S, 4S vs 2R, 4R).

Preparation I 3S,5S-(−)-3-Hydroxy-1-methyl-5-(3-pyridyl)-2-pyrrolidinone and 3S,5R-(+)-3-hydroxy-1-methyl-5-(3-pyridyl)-2-pyrrolidinone. To a stirring solution of 22.2 g (0.22 mol) of diisopropylamine in 900 mL of anhyd Et$_2$O at −75° C. was added 63.9 g (0.22 mol) of n-butyllithium in hexane (22% w/w) over 10 min while keeping the temperature below −70° C. The reaction solution was stirred for 15 min at −75° C. and then 17.6 g (0.1 mol) S-(−)-cotinine in 20 mL anhyd tetrahydrofuran was added over 10 min keeping the temperature below −70° C. After stirring for 35 min at −75° C., oxygen was bubbled into the reaction mixture. During the first 20 min of oxygen introduction, the flow was regulated on and off so as to keep the temperature of the reaction mixture below −70° C. Oxygen flow was then continued for 25 min at −75° C. and then over the next 1.5 hr after the cooling bath was removed and while the reaction mixture warmed to room temperature. The reaction mixture was poured into 200 mL of iced 10% aqueous HCl. The resulting mixture (pH2) was treated with solid sodium sulfite until it gave a negative test for peroxides. The Et$_2$O layer was separated and washed with 10% aqueous HCl. The combined acid layers were cooled in ice and basified (pH 8) with solid sodium carbonate. The basic solution was then continuously extracted under N$_2$ atmosphere with CH$_2$Cl$_2$ for 48 hr. The CH$_2$CL$_2$ was dried (Na$_2$SO$_4$) and removed to leave 17.74 g of a dark oil. Column chromatography (silica gel, CHCl$_3$—7.5% EtOH/CHCl$_3$) gave 6.7 g 3RS, 5S-3-hydroxy-1-methyl-5-(3-pyridyl)-2-pyrrolidinone. NMR showed this to be approximately a 50:50 mixture of the 3R and 3S isomers. Preparative HPLC (silica gel, 5% EtOH/CHCl$_3$) gave 3S,5S-(−)-3-hydroxy-1-methyl-5-(3-pyridyl)-2-pyrrolidinone: [α]$_{546}^{20.0}$=−32.3°±0.7° (c=0.30, MeOH); NMR (CDCl$_3$) δ 1.92 (m, 1, 4-H), 2.66 (s, 3, NCH$_3$), 2.88 (m, 1, 4-H), 3.58 (br s, 1, OH), 4.46 (m, 3, 3- and 5-H), 7.35 (m, 1, 5-pyridyl H), 7.70 (m, 1, 4-pyridyl H), 8.62 (m, 2, 2- and 6-pyridyl H) and 3S,5R-(+)-3-hydroxy-1-methyl-5-(3-pyridyl)-2-pyrrolidinone: [α]$_{546}^{20.0}$=+44.0°±0.6° (c=0.32, MeOH); NMR (CHCl$_3$) δ 2.43 (m, 2, 4-CH$_2$), 2.76 (s, 3, NCH$_3$), 3.60 (br s, 1, OH), 4.64 (m, 2, 3- and 5-H), 7.34 (m, 1, 5-pyridyl H), 7.48 (m, 1, 4-pyridyl H), 8.57 (m, 2, 2- and 6-pyridyl H).

Preparation II

3RS,5S-3-Carbethoxy-1-methyl-5-(3-pyridyl)-2-pyrrolidinone. A stirring mixture of 30.8 g (0.175 mol) S-(−)-cotinine, 82.6 g (0.7 mol) diethyl carbonate, 9.25 g (0.385 mol) of sodium hydride and 500 mL of benzene under a N$_2$ atmosphere was heated under reflux until gas evolution ceased (ca. 3 days). The mixture was cooled in ice and poured into 400 mL of cold 10% aqueous HCl. The organic layer was separated and washed with 10% aqueous HCl. The combined aqueous acid fractions were washed with CH$_2$Cl$_2$, cooled in ice and basified (pH 7–8) with solid sodium bicarbonate. The basic mixture was extracted with CH$_2$Cl$_2$. The CH$_2$Cl$_2$ was dried (Na$_2$SO$_4$) and removed to give 40.5 g of an oil which was a mixture of starting material and product. Preparative HPLC (10% EtOH/EtOAc on silica gel) gave 11.0 g S-(−)-cotinine and 22.6 g 3RS,-5S-3-carbethoxy-1-methyl-5-(3-pyridyl)-2-pyrrolidinone as a yellow oil: NMR (CDCl$_3$) δ 1.34 (t, 3, CH$_2$CH$_3$, J=7 Hz), 2.68 (s, NCH$_3$, one isomer), 2.74 (s, NCH$_3$, one isomer, 3H for 2.68 and 2.74 combined), 2.53 (m, 2, 4-CH$_2$), 3.64 (m, 1, 3-H), 4.29 (q, 2, CH$_2$CH$_3$, J=7 Hz), 4.69 (m, 1, 5-H), 7.38 (m, 1, 5-pyridyl H), 7.67 (m, 1, 4-pyridyl H), 8.58 (m, 2, 2- and 6-pyridyl H).

3S,5S-(−)-3-Carbethoxy-1-methyl-5-(3-pyridyl)-2-pyrrolidinone. To 4.0 g (16.9 mmol) of 3RS,5S-3-carbethoxy-1-methyl-5-(3-pyridyl)-2-pyrrolidinone (Prep. II) was added 25 mL of anhyd Et$_2$O. A white solid immediately began to separate. The mixture was stirred overnight. The solid was collected by filtration and washed with cold anhyd Et$_2$O. The solid was slurried with 20 mL of anhyd Et$_2$O for 10 min., collected by filtration and washed with a small amount of Et$_2$O to give 0.66 g of analytically pure 3S,5S-(−)-3-carbethoxy-1-methyl-5-(3-pyridyl)-2-pyrrolidinone: mp 72.75°–73.75° C.; [α]$_{546}^{20.0}$=−2.81°±0.08° (c=2.5. CHCl$_3$); NMR (CDCl$_3$) δ 1.32 (t,3,CH$_2$CH$_3$,J=7 Hz), 2.33 (m,1,3-H), 2.43 (q,2,CH$_2$CH$_3$,J=7 Hz), 2.66 (s,3,NCH$_3$), 2.79 (m,1,4-H), 3.59 (m,1,3-H), 4.55 (m,1,5-H), 7.41 (m,1,5-pyridyl H), 7.75 (m,1,4-pyridyl H), 8.63 (m,2,2- and 6-pyridyl H).

Preparation IV

3RS,5S-3-Carbethoxy-1,3-dimethyl-5-(3-pyridyl)-2-pyrrolidinone. To a stirring slurry of 0.6 g (0.022 mol) of sodium hydride in 40 mL of anhyd tetrahydrofuran cooled in an ice bath and under a N$_2$ atmosphere was slowly added 5.0 g (0.02 mol) of 3RS,5S-3-carbethoxy-1-methyl-5-(3-pyridyl)-2-pyrrolidinone (Prep. II) in 10 mL of anhyd tetrahydrofuran. The resulting mixture was stirred for 20 min in the cold. Small portions of sodium hydride were then added until no further gas evolution was noted. To the cooled reaction mixture was added 2.84 g (0.022 mol) of iodomethane. The reaction mixture was stirred in the cold for 3 hr and at room temperature for 1 hr. It was then poured into 50 mL of 5% aqueous HCl. The resulting acidic mixture (pH2) was extracted with CH$_2$Cl$_2$. The CH$_2$ Cl$_2$was washed with 10% aqueous HCl. The combined acid fractions were cooled in ice, basified (pH8–9) with sodium carbonate and extracted with CH$_2$Cl$_2$. The CH$_2$Cl$_2$ was dried (Na$_2$SO$_4$) and removed to give 3.88 g of 3RS,5S-3-carbethoxy-1,3-dimethyl-5-(3-pyridyl)-2-pyrrolidinone. TLC showed only a single component and NMR indicated two isomers with a combined purity >99%. The product was used as such for subsequent reaction: NMR (CDCl$_3$)δ 1.29 (t,CH$_2$CH$_3$,J=7 Hz, one isomer), 1.31 (t,CH$_2$CH$_3$,J=7 Hz, one isomer, 3H for 1.29 and 1.31 combined), 2.49 (m,2,4-CH$_2$), 2.73 (s,3,NCH$_3$), 4.22 (q,CH$_2$CH$_3$,J=7 Hz, one isomer), 4.23 (q,CH$_2$CH$_3$, J=7 Hz, one isomer, 2H for 4.22 and 4.23 combined), 4.64 (m,1,5-H), 7.41 (m,1,5-pyridyl H), 7.71 (m,1,4-pyridyl H), 8.63 (m,2,2- and 6-pyridyl H).

Preparation V

3RS,5S-1,3-Dimethyl-5-(3-pyridyl)-pyrrolidinone. A solution of 3.0 g (11.5 mmol) of 5S-3-carbethoxy-1,3-dimethyl-5-(3-pyridyl)-2-pyrrolidinone (Prep. IV) in 25 mL of 10% aqueous HCl was placed in a 125 mL Parr bomb under a $N_2$ atmosphere. The bomb was heated in an oven at 165° C. for 16 hr. The bomb was cooled (<5° C.) and opened. The reaction solution was removed. The solution was basified in the cold (<5° C.) with 50% aqueous NaOH (pH 11–12). The aqueous mixture was extracted with $CH_2Cl_2$ (4×40 mL). The $CH_2Cl_2$ was dried ($Na_2SO_4$) and removed to yield 2.0 g of 3RS-5S-1,3-dimethyl-5-(3-pyridyl)-2-pyrrolidinone as a dark oil of sufficient purity for subsequent reaction. Both TLC and GLC showed no impurities. An analytically pure sample was obtained by preparative GLC: NMR ($CD_2Cl_2$) δ 1.08 (d,4-$CH_3$, J=7.5 Hz, one isomer), 1.22 (d,4-$CH_3$,J=7.5 Hz, one isomer, 3H for 1.08 and 1.22 combined), 2.04 (extended m,3,3-,4- and 4-H), 2.55 (s,N$CH_3$, one isomer), 2.63 (d,N$CH_3$,J=0.5 Hz, one isomer, 3H for 2.55 and 2.63 combined), 4.35 (m,1,5-H), 7.44 (m,2,4- and 5-pyridyl H), 8.33 (m,2,2- and 6-pyridyl H).

Preparation VI

S-(−)-5-(3-Pyridyl)-1,3,3-trimethyl-2-pyrrolidinone. To a stirring solution of 1.22 g (12.1 mmol) of diisopropylamine in 45 mL of anhyd $Et_2O$ under a $N_2$ atmosphere was added 7.6 mL (12.1 mmol) of 1.6 M n-butyllithium in hexane. The solution was stirred for 10 min, cooled in ice and 1.15 g (6.05 mmol) of 3RS,5S-1,3-dimethyl-5-(3-pyridyl)-2-pyrrolidinone (Prep. V) (previously dried in anhyd $Et_2O$ over $CaCl_2$) in 5 mL of anhyd $Et_2O$ was added slowly over 10 min, keeping the temperature of the reaction mixture near 5° C. The reaction mixture was allowed to stir in the cold for 30 min. To the mixture was then slowly added 1.63 g (11.5 mmol) of iodomethane while maintaining the reaction mixture temperature near 5° C. The reaction mixture was stirred for 30 min in the cold, warmed to room temperature and stirred for 30 min. To the ice cooled reaction mixture was added 10 mL $H_2O$. The mixture was acidified (pH2) with 10% aqueous HCl. The $Et_2O$ layer was separated and washed with 5 mL of 10% aqueous HCl. The combined aqueous acid layers were washed with $CH_2Cl_2$ (2×20 mL), cooled (<5° C.) and basified (pH11–12) with 50% aqueous NaOH. The basic mixture was extracted with $CH_2Cl_2$ (4×30 mL). The $CH_2Cl_2$ was dried ($Na_2SO_4$) and removed to leave 1.05 g of S-(−)-5-(3-pyridyl)-1,3,3-trimethyl-2-pyrrolidinone sufficiently pure for subsequent reaction: mp85°–97° C. Sublimation [55°–65° C. (0.02 mm/Hg)] followed by recrystallization from hexane gave analytically pure S-(−)-5-(3-pyridyl)-1,3,3-trimethyl-2-pyrrolidinone: mp 96°–100° C.; $[\alpha]_{546}^{20.0} = -44.30° \pm 0.71°$ (c=0.28, $CHCl_3$); NMR ($CDCl_3$) δ 1.22 (s,3,3-$CH_3$), 1.28 (s,3,3-$CH_3$), 1.66 (m,1,4-H), 2.37 (m,1,4-H), 2.69 (s,3,N$CH_3$), 4.52 (m,1,5-H), 7.38 (m,1,5-pyridyl H), 7.65 (m,1,4-pyridyl H), 8.62 (m,2,2- and 6-pyridyl H).

EXAMPLE 1

2S,4S-(−)-4-Hydroxy-1-methyl-2-(3-pyridyl)pyrrolidine and 2S,4R-(−)-4-hydroxy-1-methyl-2-(3-pyridyl)-pyrrolidine. To an ice bath cooled, stirring solution of 1.0 g (5.2 mmol) of 3RS,5S-3-hydroxy-1-methyl-5-(3-pyridyl)-2-pyrrolidinone (Prep. I) in 15 mL of anhyd tetrahydrofuran under a $N_2$ atmosphere was added slowly 21.5 mL (52 mmol) of 0.98 M borane in tetrahydrofuran. The resulting reaction solution was heated under reflux for 16 hr, cooled in ice, slowly acidified (pH2) with 10% aqueous HCl and heated under reflux and a $N_2$ atmosphere for 6 hr. The reaction solution was cooled and the tetrahydrofuran removed under reduced pressure. The remaining aqueous acid mixture was cooled (>5° C.), basified (pH11–12) with excess 50% aqueous NaOH and continuously extracted with $Et_2O$ for 16 hr. The $Et_2O$ was dried (NaOH) and removed to give 0.87 g of 2S,4RS-4-hydroxy-1-methyl-2-(3-pyridyl)pyrrolidine. NMR showed this to be approximately a 50:50 mixture of the 4S and 4R isomers. TLC (85:14:1; $CHCl_3$:EtOH:$NH_4OH$) showed the 4R isomer at $R_f$0.27 and 4S isomer at $R_f$0.37. The isomers were separated by preparative TLC (solvent system as above). The 4S isomer was distilled giving product as a light yellow oil with purity >98% as shown by GLC: bulb to bulb distillation [oven temperature 80°–130° C. (0.04 mm/Hg)]. An analytically pure sample was obtained by preparative GLC: $[\alpha]_{546}^{20.0} = -159.37° \pm 0.8°$ (c=0.25, $CHCl_3$); NMR ($CD_2Cl_2$) δ 1.76 (m,1,3-H), 2.08 (s,3,N$CH_3$), 2.55 (m,2,3- and 5-H), 3.13 (m,2,2- and 5-H), 3.73 (s,1,OH), 4.32 (m,1,4-H), 7.17 (m,1,5-pyridyl H), 7.80 (m,1,4-pyridyl H), 8.49 (m,2,2- and 6-pyridyl H). The 5R isomer was distilled giving product as a light yellow oil with purity >98% as shown by GLC: bulb to bulb distillation [oven temperature 68°–137° C. (0.035 mm/Hg)]. An analytically pure sample was obtained by preparative GLC: $[\alpha]_{546}^{20.0} = -219.46 \pm 0.67°$ (c=0.3, $CHCl_3$); NMR ($CDCl_3$) δ1.91 (m,2,3- and 3-H or 3- and 5H) 2.01 (s,3,N$CH_3$), 2.26 (m,1,3-H or. 5-H), 3.39 (m,2,2- and 5-H), 4.30 (s,1,OH), 4.40 (m,1,4-H), 7.18 (m,1,5-pyridyl H), 7.63 (m,1,4-pyridyl H), 8.38 (m,2,2- and 6-pyridyl H).

EXAMPLE 2

2S,4S-(−)-4-Hydroxymethyl-1-methyl-2-(3-pyridyl)-pyrrolidine and 2S,4R-(−)-4-hydroxymethyl-1-methyl-2-(3-pyridyl)pyrrolidine. To an ice cooled, stirring solution of 12.4 g (0.05 mol) of 3RS,5S-3-carbethoxy-1-methyl-5-(3-pyridyl)-2-pyrrolidinone (Prep. II) in 75 mL of anhyd tetrahydrofuran under a $N_2$ atmosphere was added 240 mL (0.24 mol) of 1.0 M boran in tetrahydrofuran. The resulting solution was heated under reflux for 16 hr, cooled in ice and cautiously acidified with 75 mL of 10% aqueous HCl (pH2). The resulting mixture was heated under reflux and a $N_2$ atmosphere for 6 hr. The tetrahydrofuran was removed under reduced pressure and the resulting mixture washed with $CH_2Cl_2$. The aqueous acid was cooled (<5° C.), basified (pH11–12) with excess 50% aqueous NaOH and extracted with $Et_2O$. The $Et_2O$ was dried (NaOH) and removed to leave 8.4 g of a light yellow oil. NMR showed the oil to be approximately a 50:50 mixture of the 4S and 4R isomers of 2S,4RS-4-hydroxymethyl-1-methyl-2-(3-pyridyl)pyrrolidine. TLC (85:14:1; $CHCl_3$:EtOH:$NH_4OH$) showed the 4R isomer at $R_f$0.32 and the 4S isomer at $R_f$0.43. The isomers were separated by preparative TLC (135:14:1.5; $CHCl_3$:EtOH:$NH_4OH$); developed twice. The 2S,4S-4-hydroxymethyl-1-methyl-2-(3-pyridyl)pyrrolidine was obtained as a yellow oil. TLC showed only one component and GLC indicated purity >98%. An analytically pure sample was obtained by GLC: $[\alpha]_{546}^{20.0} = -153.6° \pm 0.8°$ (c—0.25, $CHCl_3$); NMR ($CDCl_3$) δ1.63 (m,1,3-H), 2.18

(s,3,NCH$_3$), 2.49 (m,3,3-4- and 5-H), 3.19 (m,2,2- and 5-H), 3.68 (s,1,OH), 3.70 (d,2, CH$_2$O,J—4 Hz), 7.29 (m,1,5-pyridyl H), 7.55 (m,1,4-pyridyl H), 8.27 (m,2,2- and 6-pyridyl H). The 2S,4R-4-hydroxymethyl-1-methyl-2-(3-pyridyl)pyrrolidine was obtained as a yellow oil. TLC showed only one component and GLC indicated purity >98%. An analytically pure sample was obtained by GLC: [α]$_{546}^{20.0}$=−184.5°±0.4° (c=0.2, CHCl$_3$); NMR (CDCl$_3$) δ2.18 (s,3,NCH$_3$), 2.33 (m,4,3-3-,4- and 5-H), 3.33 (m,2,2- and 5-H), 3.68 (d,2, CH$_2$O,J=6 Hz), 4.15 (s,1,OH), 7.28 (m,1,5-pyridyl H), 7.53 (m,1,4-pyridyl H), 8.12 (m,2,2- and 6-pyridyl H).

EXAMPLE 3

2S,4S-(−)-1,4-Dimethyl-2-(3-pyridyl)pyrrolidine. To a stirring slurry of 0.12 g (4.7 mmol) of sodium hydride in 40 mL of anhyd 1,2-dimethoxyethane under a N$_2$ atmosphere was added slowly 0.45 g (2.3 mmol) of 2S,4S-(−)-4-hydroxymethyl-1-methyl-2-(3-pyridyl)-pyrrolidine (Ex. 2). After stirring for 6 hr, the mixture was treated with 0.67 g (3.4 mmol) of p-toluenesulfonyl chloride and stirred for 20 hr. To the reaction mixture was then slowly added 0.89 g (23.4 mmol) of lithium aluminum hydride and stirring continued for 48 hr. Water was added slowly to decompose the unreacted lithium aluminum hydride. The inorganic salts were removed by filtration and washed with excess Et$_2$O. The filtrate and washings were combined, dried (NaOH) and concentrated under reduced pressure to leave a dark oil. Preparative TLC purification of the oil (acetone, two elutions) gave 0.05 g of 2S,4S-(−)-1,4-dimethyl-2-(3-pyridyl)pyrrolidine. GLC showed purity >98%. Preparative GLC gave analytically pure product: [α]$_{546}^{20.0}$=−236.48°±0.91° (c=0.219,CHCl$_3$); NMR (CD$_2$Cl$_2$) δ1.00 (d,3,4-CH$_3$,J=7 Hz), 1.63 (m,1,3-H), 2.06 (s,3,NCH$_3$), 2.79 (m,3,3-,4- and 5-H), 2.96 (m,1,5-H), 3.34 (m,1,2-H), 7.24 (m,1,5-pyridyl H), 7.68 (m,1,4-pyridyl H), 8.49 (m,2,2- and 6-pyridyl H).

EXAMPLE 4

2S,4R-(−)-1,4-Dimethyl-2-(3-pyridyl)pyrrolidine was prepared from 2S,4R-(−)-4-hydroxymethyl-1-methyl-2-(3-pyridyl)pyrrolidine (Ex. 2) using the method described for the synthesis of 2S,4S-(−)-1,4-dimethyl-2-(3-pyridyl)pyrrolidine (Ex. 3). Analytically pure product was obtained by preparative TLC: [α]$_{546}^{20.0}$=−170.59°±0.78° (c=0.257,CHCl$_3$); NMR (CD$_2$Cl$_2$) δ1.01 (d,3,4-CH$_3$,J=7 Hz), 1.86 (m,3,3-,3- and 4-H), 2.09 (s,3,NCH$_3$), 2.33 (m,1,5-H), 3.23 (m,2,2- and 5-H), 7.23 (m,1,5-pyridyl H), 7.61 (m,1,4-pyridyl H), 8.48 (m,2,2- and 6-pyridyl H).

EXAMPLE 5

S-(−)-2-(3-Pyridyl)-1,4,4-trimethylpyrrolidine. To a stirring solution of 1.05 g (5.1 mmol) S-(−)-5-(3-pyridyl)-1,3,3-trimethyl-2-pyrrolidinone (Prep. VI) in 40 mL of anhyd tetrahydrofuran under a N$_2$ atmosphere was added slowly 17.9 mL (17.9 mmol) of 1 M borane in tetrahydrofuran. The reaction solution was heated under reflux for 16 hr, cooled to room temperature and cautiously acidified (pH2) with 25 mL of 10% aqueous HCl. The resulting solution was heated under reflux under a N$_2$ atmosphere for 6 hr. The tetrahydrofuran was removed under reduced pressure. The acidic mixture was diluted with 20 mL H$_2$O and washed with CH$_2$Cl$_2$ (2×16 mL). The aqueous layer was basified (pH11-12) in the cold (<5° C.) with excess 50% aqueous NaOH and extracted with Et$_2$O (4×50 mL). The Et$_2$O was dried (NaOH) and removed to leave 0.83 g of an amber oil. Distillation of the oil gave 0.70 g of S-(−)-2-(3-pyridyl)-1,4,4-trimethylpyrrolidine: bp 44°–46° C. (0.015 mm/Hg). GLC showed purity >98%. Redistillation gave analytically pure material: [α]$_{546}^{20.0}$=−221.36°±0.44° (c=0.5, CHCl$_3$); NMR (CDCl$_3$) δ1.34 (s,3,4-CH$_3$), 1.39 (s,3,4-CH$_3$), 1.58 (m,1,3-H), 2.03 (m,1,3-H), 2.16 (s,3,NCH$_3$), 2.20 (m,1,5-H), 3.0 (m,1,5-H), 3.28 (m,1,2-H), 7.33 (m,1,5-pyridyl H), 7.8 (m,1,4-pyridyl H), 8.59 (m,2,2- and 6-pyridyl H).

EXAMPLE 6

Ethanol solutions having concentrations of 0.1% and 0.2% of the candidate compounds were prepared. A nicotine sulfate control was prepared using the same concentrations, which are less than those that would cause "100% kill" in order to provide a comparative profile of the candidate compounds. Exploratory screenings with 0.5% concentrations of the candidate compounds conducted against *E. elutella* larvae achieved almost 100% kill in all cases (excluding the solvent control).

Filter paper discs, 0.15 mm in diameter, received 0.01 ml. of the prepared (diluted) test compound. Each disc was placed at the bottom of a 10 ml. clear plastic vial. After the disc had air dried to eliminate the ethanol, one larva of *E. elutella* (2nd–4th instar stage) was placed within the individual vial. This vial was then closed by the insertion of a smaller vial that acted as a piston, and that reduced the free air space to a 2–3 ml. volume. Each dosage employed was replicated three times. Observations and results were recorded at the end of about 24 hours following treatment. Results (number of dead larvae/three replicates) are shown in the following table.

| Compound or Treatment | 0.1% Treatment | 0.2% Treatment |
|---|---|---|
| 2S,4S—(−)-4-Hydroxymethyl-1-methyl-2-(3-pyridyl)-pyrrolidine | 1 | 1 |
| 2S,4R—(−)-4-Hydroxymethyl-1-methyl-2-(3-pyridyl)-pyrrolidine | 0/3 | 1 |
| 2S,4S—(−)-1,4-Dimethyl-2-(3-pyridyl)pyrrolidine | 1 | 1 |
| 2S,4R—(−)-1,4-Dimethyl-2-(3-pyridyl)pyrrolidinne | 1/3 | 1 |
| (−)-Nicotine | 1 | 3/3 |
| Solvent control (EtOH) | 0/3 | 0/3 |
| S—(−)-1,4,4-Trimethyl-2-(3-pyridyl)pyrrolidine | 1/3 | 1 |
| 2S,4R—(−)-4-Hydroxy-1-methyl-2-(3-pyridyl)pyrrolidine | 1/3 | 0/3 |
| 2S,4S—(−)-4-Hydroxy-1-methyl-2-(3-pyridyl)pyrrolidine | 1/3 | 0/3 |
| Nicotine Sulfate | 0/3 | 1 |
| Untreated Control | 0/3 | |

It is noted that the concentrations of candidate compounds employed in these preparations (0.1% and 0.2%) are much higher than the 0.04% concentration generally used when nicotine sulfate is employed in the field as a contact insecticide against aphids and other Heteroptera. However, larvae of the Lepidoptera (such as the tobacco moth employed in this example) are known to require higher concentrations of nicotine sulfate to be controlled.

What is claimed is:

1. Optically pure S-(−)-2-(3-pyridyl)-1,4,4-trimethylpyrrolidine.
2. Optically pure R-(+)-2-(3-pyridyl)-1,4,4-trimethylpyrrolidine.
3. Optically pure 2S,4S-(−)-1,4-dimethyl-2-(3-pyridyl)pyrrolidine.
4. Optically pure 2R,4R-(+)-1,4-dimethyl-2-(3-pyridyl)pyrrolidine.
5. Optically pure 2R,4S-(+)-1,4-dimethyl-2-(3-pyridyl)pyrrolidine.
6. Optically pure 2S,4R-(−)-1,4-dimethyl-2-(3-pyridyl)pyrrolidine.
7. Optically pure S-(−)-5-(3-pyridyl)-1,3,3-trimethyl-2pyrrolidinone.
8. Optically pure R-(+)-5-(3-pyridyl)-1,3,3-trimethyl-2-pyrrolidinone.

* * * * *

UNITED STATES PATENT AND TRADEMARK OFFICE
CERTIFICATE OF CORRECTION

PATENT NO. : 4,452,984
DATED : June 5, 1984
INVENTOR(S) : William B. Edwards

It is certified that error appears in the above-identified patent and that said Letters Patent is hereby corrected as shown below:

Column 1, line 59, "continine" should be --cotinine--. Column 1, line 60, "cities" should be --cited--.
Column 5, line 18, "(2R,4S)" should be --(2S,4S)--.
Column 6, line 60, should read

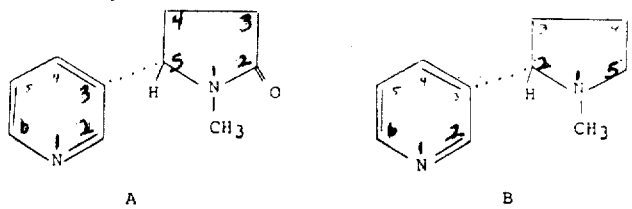

rather than

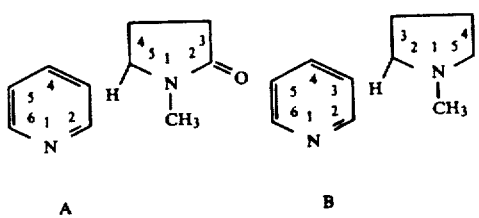

Column 7, line 46, "CH2CL2" should read --CH2Cl2--.

Signed and Sealed this

Sixteenth Day of April 1985

[SEAL]

Attest:

DONALD J. QUIGG

Attesting Officer Acting Commissioner of Patents and Trademarks